(12) United States Patent
Tang et al.

(10) Patent No.: US 12,364,828 B2
(45) Date of Patent: Jul. 22, 2025

(54) BLOWER FOR RESPIRATOR DEVICE (71) Applicant: SYSMED (CHINA) CO., LTD, Liaoning (CN)

(72) Inventors: Zhuoran Tang, Sydney (AU); Yong Huang, Liaoning (CN); Yongquan Zhu, Liaoning (CN); Wenxiu Shu, Liaoning (CN); Jiaping Fu, Liaoning (CN); Hongliang Bian, Liaoning (CN); Feng Long, Liaoning (CN); Feng Chen, Liaoning (CN); Bo Wang, Liaoning (CN); Yue Jian, Liaoning (CN); Hailong Guo, Liaoning (CN)

(73) Assignee: SYSMED (CHINA) CO., LTD, Liaoning (CN)

( * ) Notice: Subject to any disclaimer, the term of this patent is extended or adjusted under 35 U.S.C. 154(b) by 1148 days.

(21) Appl. No.: 17/220,881

(22) Filed: Apr. 1, 2021

(65) Prior Publication Data
US 2021/0220585 A1 Jul. 22, 2021

Related U.S. Application Data (63) Continuation-in-part of application No. PCT/CN2019/094559, filed on Jul. 3, 2019.

(30) Foreign Application Priority Data

Jun. 6, 2019 (CN) .......................... 201910491187.2

(51) Int. Cl.
A61M 16/00 (2006.01)
A61M 16/10 (2006.01)
(Continued)

(52) U.S. Cl.
CPC .... A61M 16/0066 (2013.01); A61M 16/1075 (2013.01); F04D 25/082 (2013.01);
(Continued)

(58) Field of Classification Search
CPC . A61M 16/0066–0069; A61M 16/1075–1095; A61M 2205/3368;
(Continued)

(56) References Cited

U.S. PATENT DOCUMENTS

| 2008/0310978 A1* | 12/2008 | Hoffman | ........... A61M 16/0063 415/203 |
| 2011/0027078 A1* | 2/2011 | Pan | ........................ F04D 25/082 415/206 |

(Continued)

FOREIGN PATENT DOCUMENTS

| CN | 105298880 A | 2/2016 |
| CN | 105604964 A | 5/2016 |
| CN | 205287146 U | 6/2016 |
| CN | 106422017 A | 2/2017 |
| CN | 109806471 A | 5/2019 |

*Primary Examiner* — Rachel T Sippel
(74) *Attorney, Agent, or Firm* — NKL Law; Allen Xue (57) ABSTRACT

A pressurized treatment gas supply device has a lower enclosure and an upper enclosure. The air outlet is formed by part of the upper enclosure and lower enclosure and the gas outlet direction is tangent to the outer surface of the enclosure. The lower enclosure is has an annular wall and an outer wall. The space between the outer wall and the upper enclosure wall forms a gas path leading to the gas outlet. A motor is located on the inner side of the lower enclosure. The output shaft end of motor is arranged on the lower enclosure and output shaft of the motor is connected to an impeller. An gas inlet structural member is arranged on the lower enclosure, the end that opposite to impeller is axial air inlet end. The noise silencing chamber is formed between the top of air inlet structural member and the annular frame.

20 Claims, 9 Drawing Sheets (51) Int. Cl.
*F04D 25/08* (2006.01)
*F04D 29/28* (2006.01)
*F04D 29/42* (2006.01)
*F04D 29/66* (2006.01)

(52) U.S. Cl.
CPC ....... *F04D 29/281* (2013.01); *F04D 29/4206* (2013.01); *F04D 29/664* (2013.01); *F04D 29/665* (2013.01); *A61M 2205/3368* (2013.01); *A61M 2205/42* (2013.01)

(58) Field of Classification Search
CPC ............ A61M 2205/42; F04D 25/0606; F04D 25/08–082; F04D 29/281–282; F04D 29/30; F04D 29/4206; F04D 29/4226; F04D 29/441; F04D 29/023; F04D 29/083; F04D 29/58; F04D 29/582; F04D 29/601; F04D 29/66–661; F04D 29/663; F04D 29/665–668; F04D 1/00; F04D 17/16
See application file for complete search history.

(56) References Cited

U.S. PATENT DOCUMENTS

| | | | |
|---|---|---|---|
| 2012/0067347 A1 | 3/2012 | Bothma | |
| 2015/0003966 A1* | 1/2015 | Duquette | F04D 29/667 415/206 |
| 2016/0138611 A1* | 5/2016 | Teramoto | F04D 29/056 417/423.8 |
| 2016/0290352 A1* | 10/2016 | Hayamitsu | F04D 25/02 |
| 2017/0097013 A1* | 4/2017 | Wall, II | B62D 35/001 |

* cited by examiner

BLOWER FOR RESPIRATOR DEVICE

FIELD OF THE INVENTION

The invention relates to a pressurized treatment gas supply device, in particular to a blower for respirator.

This invention relates to a pressurized gases supply apparatus, particularly but not solely for providing respiratory assistance to patients or users who require a supply of gas at variable positive pressure for the treatment of diseases such as Chronic Obstructive Pulmonary Disease (COPD), Obstructive Sleep Apnea (OSA), snoring, and the like or life support ventilator. In particular, this invention relates to a compressor or blower for use in a gases supply apparatus which in use is integral with the gases supply apparatus. However, the blower and gases supply apparatus may be used in other applications where similar requirements are the demand (e.g. medical or otherwise).

BACKGROUND OF THE INVENTION

Respirator is a device that can replace, control or change people's normal physiological breathing, increase lung ventilation, improve respiratory function, reduce respiratory consumption, and save cardiac reserves.

As the source of treatment gas, blower is the core part of the respirator. The blower in the respirator supplies gas that has certain amount of pressure and flow to the patient. The performance parameters of the blower affects the performance of the respirator directly, so it is necessary to design the blower with the detailed consideration for the aspects of mounting, shock absorption, noise reduction, air flow path, air flow regulation and structure.

CPAP (Continuous Positive Airway Pressure) respirator is mainly used for the treatment of sleep apnea syndrome, that is, severe snoring and associated symptoms of breath obstruction, and it can also treat the complications of sleep apnea, increase the blood oxygen concentration during the user's night sleep, and treat hypoxemia. Sleep respirator is mainly used during the patient's sleep period, so it has particularly high demand for noise reduction. At present, the respirator on the market usually uses general-purpose blower, there are serious problems such as easy to produce turbulence, low efficiency and high noise. The impeller is driven by a motor to rotate at high speed to generate a certain flow of air in the volute airway, and at the same time, the gas is maintained in a certain pressure range in the volute airway. During this process, large noise could be generated, which mainly comes from three aspects. An aspect of the noise caused by the air flowing through the impeller with high speed rotation. The second aspect, the aerodynamic noise caused by the air flowing at high speed in the volute. The third aspect, the vibration noise caused by the motor with high speed rotation.

Bi-level respirator is the most widely used respirator for non-invasive nasal mask mechanical ventilation. It is used in all kinds of the pulmonary disease caused by acute or chronic respiratory failure, such as Chronic Obstructive Pulmonary Disease (COPD), bronchiectasis, cystic fibrosis, and interstitial lung disease, heart failure, neuromuscular disease, obesity hypoventilation etc. As well as various types of sleep respiratory diseases, especially central sleep apnea or complex sleep apnea patients. In order to achieve the therapeutic effect of respirator, it is necessary to detect the patient's breath through the control system to ensure that the respirator can follow the patient's respiratory event accurately, which requires the continuous acceleration and deceleration of the blower to achieve rapid response. During the rapid acceleration and deceleration, the blower will generate a large amount of heat. If the heat cannot be dissipated in time, the temperature of the motor will rise significantly, which will affect the electrical safety and the blower life. The issue of blower heat dissipation has always been a key problem to be solved in the design process of blower. At present, the blowers adopted by the respirator in the market are mainly motors on the outside of the blower volute housing. During operation, the air cannot flow through the motor, so additional design consideration are needed to remove the heat of motor itself. The additional heat dissipation structure design not only increases the demand for internal space, but also the result is not ideal. There is also a design form of motor in the air duct of the blower on the market, but all of them are axial air outlet form, and the structure is relatively complex, the motor also needs special customization, not commonly available. Therefore, it is valuable to provide a new blower design approach to solve the above problems.

At present, high pressure, high flow rate, fast response, high reliability, low noise, compact structure, economical and effective design of respiratory gas pressure source (blower) for respirator has become a demand.

SUMMARY OF INVENTION

It is an object of the present invention to provide a blower that meets the needs identified above. This enables the blower to be used in a range of applications where fast response time, easy to drive and control, high output pressure, high flow output, high reliability, low noise, small in size and cost effective are desirable, such as in bi-level respiratory treatment apparatus.

An aspect of the disclosed technology relates to respiratory gases supply apparatus system, methods of use and devices structured to at least capable to supply adequate prescribed treatment pressure to the patient.

An aspect of the disclosed technology relates to respiratory gases supply apparatus system, methods of use and devices structured to at least capable to supply adequate prescribed treatment pressure variation speed to the patient.

An aspect of the disclosed technology relates to respiratory gases supply apparatus system, methods of use and devices structured to at least capable to supply adequate gas flow at prescribed treatment pressure to the patient.

Another aspect of the disclosed technology relates to OSA treatment system, methods of use and devices structured to at least reduce generated noise, vibrations, size and bulk or combinations thereof.

Another aspect relates to bi-level devices configured to supply pressurized breathable gas (e.g., air) in a manner suitable for treatment of COPD or alike.

Another aspect relates to life support ventilator devices configured to supply pressurized breathable gas (e.g., air) in a manner suitable for treatment of severe illness are cared for in a hospital's intensive care unit (ICU).

An aspect of the disclosed technology relates to respiratory gases supply apparatus system, methods of use and devices structured to at least capable to provide the reliability required by bi-level devices or to life support ventilator devices which are under high frequency.

Another aspect of the disclosed technology relates to improvements and/or alternative examples of the blower described in USA Application No. U.S. Pat. No. 9,765,796 B2, e.g., to mitigate blower noise.

Another aspect of the disclosed technology relates to a high performance high speed motor structured to dissipate the internal heat efficiently, that enable the blower assembly remove the heat with cold air flow effectively.

Another aspect of the disclosed technology relates to a high performance high speed motor structured to have a temperature sensor and heat from all parts of the motor is able to transfer to the sensor efficiently, that enable the blower assembly be able to sense temperature from all critical parts with only one sensor.

Another aspect of the disclosed technology relates to a high efficiency very low inertia impeller structured to provide the pressure, flow, acceleration and deceleration capability that enable the blower assembly to produce required respiratory therapy.

Another aspect of the disclosed technology relates to a high efficiency very low inertia impeller assembly method to provide the pressure, flow, acceleration and deceleration capability that enable the blower assembly to produce required respiratory therapy with ensured reliability.

Disclosure of Invention

In order to meet the above demand, the objective of this invention is to provide a suitable blower to be used for respirator.

The objective of this invention is realized through the following technical approach:

The blower of the invention comprising a motor, a impeller, a lower enclosure, upper enclosure and a air inlet structure. Lower enclosure is assembled to an upper enclosure, an air outlet is formed by part of the upper enclosure and the lower enclosure. The lower end of the outer wall is open, the upper end of the outer wall are provided with an annular frame, a motor is located on the inner side of the annular wall A, the output shaft end is arranged on the lower enclosure, an output shaft of the motor is fitted with an impeller, the impeller is positioned between the space of annular frame and a top plate of the upper enclosure, an air inlet structural member arranged on the lower enclosure and part of it is in the space between the annular wall and the outer wall. A noise silencing chamber is formed between the air inlet structural member and the annular frame. The external cold air flows through air inlet structural member, and enters into the noise silencing chamber along the axial direction of the enclosure, then flows through the surface of motor for heat exchange, the air after heat exchange flows out through the described air inlet.

The air inlet structural member includes a flat plate and an air inlet. The flat plate is annular type, which is part of the lower enclosure, there are many inlet hole along with circumferential direction on the flat plate, each inlet hole has an inlet tube connected, at the bottom of the inlet tube and top of tubes, space between annular frame, annular walls forms noise silencing chamber;

The flat plate arranged with drainage holes;

The flat plate has motor support ring, this motor support ring and flat plate are used as motor supported structure of non-output shaft end.

The blower of the invention could also include motor, impeller, lower enclosure, upper enclosure and sound absorbing foam. Among them, lower enclosure is affixed to upper enclosure, the part of upper enclosure and lower enclosure forms an air outlet. The end of lower enclosure is open ends, top of it has an annular frame. The motor is located on the inner side of the lower enclosure. The motor output shaft end is arranged on the lower enclosure. The output shaft of the motor is connected to an impeller, which is positioned between the annular frame and a top plate of upper enclosure. The sound absorbing foam is arranged on the lower enclosure. The air inlet channel is formed by the sound absorbing foam and outer surface of motor. When the motor rotates, it drives the impeller, air flows through air inlet channel and through the surface of motor for heat exchange, the air after heat exchange flows out through the air outlet.

Wherein, the sound absorbing foam is made of PE or EVA open foaming.

The sound absorption coefficient of sound absorbing foam is between 0.8 to 1 when frequency is between 500 to 4 KHz.;

The length to diameter ratio of the non-shaft part of the motor rotor is between 3:1 to 6:1;

The outer housing of motor is made of heat conduction material, to transmit heat from the inside of the motor;

The tubular housing of motor is made of aluminum alloy;

The motor coil is tubular and without slot, mounted on the magnetic core of stator. The magnetic core of stator uses low loss stamped silicon steel to form slot-less sheet stacked tubule core. This magnetic core of stator is mounted on the inside of tubule motor housing.

The motor is equipped with temperature sensor. The motor housing, back cover, front cover and printed circuit board transfer heat from other parts of motor to the temperature sensor to provide a temperature signal to the control center;

The output shaft of motor has water prove washer and/or soft washer;

The impeller is made of material that has the density less than 1 g/mm$^3$;

The back plate of impeller has at least one annular protuberance which can improve the structural strength;

The impeller is directly connected to the output shaft of motor, the output shaft of motor and impeller contact part is serrated;

The air outlet of blower is on a plane different from the plane impeller blades are on;

The lower enclosure has an annular wall and an outer wall. The lower end of the annular wall and the lower end of the outer wall are open, the upper end of the annular wall and the upper end of the outer wall are provided with an annular frame, a space between the outer wall and the upper enclosure form a path to the air outlet, a motor is located on the inner side of the annular wall A, the output shaft end is arranged on the lower enclosure; The air inlet structural member is arranged between the annular wall and the outer wall.

The inner ring of the annular frame extend downward to form support ribs, two adjacent support ribs forms inlet hole A, the inner side of annular wall has motor mounting frame, which connected to support rib, the output shaft side of motor fixed on the motor mounting frame; the bottom side of outer wall outer edge forms half of outlet channel.

The upper enclosure includes annular wall, outlet channel and top plate, once annular wall is connected to the lower enclosure, it is located on the outside of outer wall of the lower enclosure, the top plate is on the top of annular wall, the bottom side is open, the part of bottom side of annular wall outer edge forms half of the outlet channel.

The annular flow channel between annular wall and outer wall has 1 to 2 degree angle relative to axial, to make the outlet path increase the air flow cross area gradually to adapt to outlet tube cross section area.

The advantages and positive effects of the present invention are:

The noise during operation is low, the structure is compact, the motor can effectively utilize cold air flow for motor heat dissipation, and able to provide the specified patients treatment pressure, flow rate.

The noise silencing chamber is formed between the air inlet structural member and the annular frame, and minimizes inlet flow noise effectively.

When the upper enclosure assembled onto the lower enclosure, the pressurized gas flow between the annular frame and top plate will rotate along with the center axis of housing, as well as move downwards to the outlet channel, so that it can eliminate noise formed by pressure fluctuations between the impeller blade and volute tongue.

This impeller has high efficiency, low inertia, provides effective pressure, flow rate, acceleration and deceleration capability, enable the blower to produce the required respiratory treatment parameters.

Both end of motor could be "soft mounted", and this arrangement can reduce non-balancing vibration of rotor and impeller transfer to the other parts of blower to prevent noise propagation, for further noise reduction.

The present invention can also employ an inlet sound-absorbing foam on the inner face of annular wall of lower enclosure, so an air inlet channel is formed between the motor surface and the air intake sound-absorbing foam, cooling the motor when the air flows through the channel at high speed, meanwhile, when the noise generated inside the volute transmit in the reverse way of the air inlet flow through the air inlet channel, the sound-absorbing foam can also reduce the back radiated noise.

Where: 1 is blower, 2 is motor, 201 is tubular motor housing, 202 is magnetic core of stator, 203 is coil, 204 is back cover, 205 is front cover, 206 is output shaft, 207 is permanent magnets, 208 is balancing ring, 209 is printed circuit board, 210 is bearing, 211 is temperature sensor, 212 is wire mount, 213 is electrical wire, 214 is Y type connected coil terminal wires, 215 is bearing preload spring;

3 is impeller, 301 is main blade, 302 is splitter blade, 303 is impeller hub, 304 is through hole, 305 is back plate, 306 is the annular protuberance;

4 is lower enclosure, 401 is annular wall A, 402 is outer wall, 403 is outlet channel A, 404 is the annular frame, 405 is the support rib, 406 is the inlet hole A, 407 is the motor mounting frame;

5 is upper enclosure, 501 is annular wall B, 502 is outlet channel B, 503 is mounting ear, and 504 is top plate;

6 is air inlet structure, 601 is the flat plate, 602 is inlet tube, 603 is drainage hole, and 604 is inlet hole B;

7 is motor support ring, 8 is noise silencing chamber, 9 is water prevent washer, 10 is soft washer, 11 is sound absorbing foam, 12 is air inlet channel, and 13 is air outlet;

Detailed Implementation

The invention is further described with the following figures.

As shown in FIGS. 1 to 11, the blower 1 in this instance includes motor 2, impeller 3, lower enclosure 4, upper enclosure 5, air inlet structure 6 and motor support ring 7, in addition, lower enclosure 4 and upper enclosure 5 assembled together and forming blower 1 housing; the part of the upper enclosure 5 with lower enclosure 4 formed air outlet 13 as well, the air flow direction of air outlet 13 is tangent to outer surface of housing.

Figure 4:
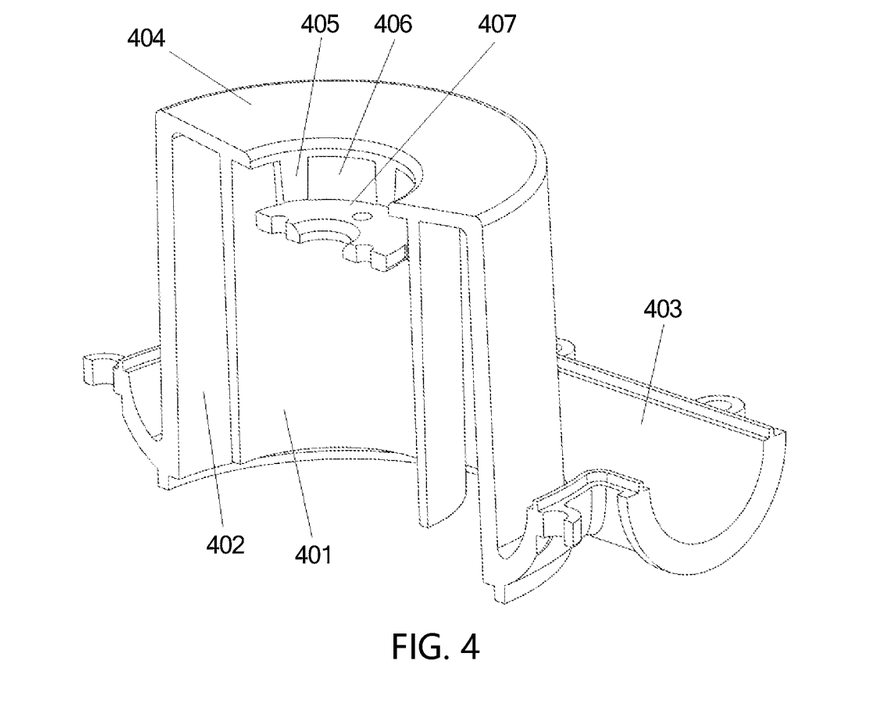
FIG. 4 is the internal structure sectional view of the lower enclosure of the present invention.

The lower enclosure 4 (from inside to outside) has annular wall 401 and outer wall 402, the bottom side of annular wall and outer wall 402 is open, on the top is annular frame 404, outer wall 402 and annular wall 401 are coaxial; the inner ring of annular frame404 extend downward to form support rib 405, two adjacent support ribs 405 forms inlet hole406, the inner side of annular wall 401 has motor mounting frame 407, which connected to support rib 405, the output shaft side of motor 2 fixed on the motor mounting frame 407; the part of bottom side of outer wall 402 forms ½ outlet 403. The space between outer wall 402 and upper enclosure 5 connect with air outlet 13. The motor 2 located inner side of annular wall 401, output shaft fixed on the motor mounting frame 407.

Figure 5:
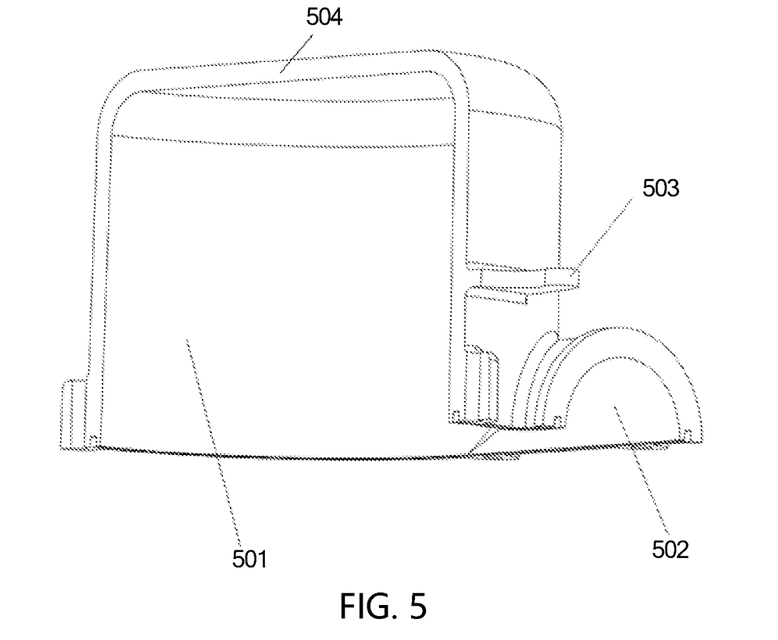
FIG. 5 is the internal structure sectional view of the upper enclosure of the present invention.

The upper enclosure 5 includes annular wall 501, outlet channel 502, mounting ear 503 and top plate 504. Once annular wall 501 is connected to the lower enclosure 4, it is located on the outside of outer wall 402, and is coaxial setting with outer wall 402, annular wall 401; the top plate 504 is on the annular wall 501, the bottom side is open, the outer surface of annular wall 501 has mounting ears 503 align to circumferential direction, the bottom side of annular wall 501 outer edge forms half of outlet channel as part of air outlet 13. The outlet channel 502 on the upper enclosure 5 close together with the outlet channel 403 on the lower enclosure forms the complete air outlet 13.

Figure 8A:
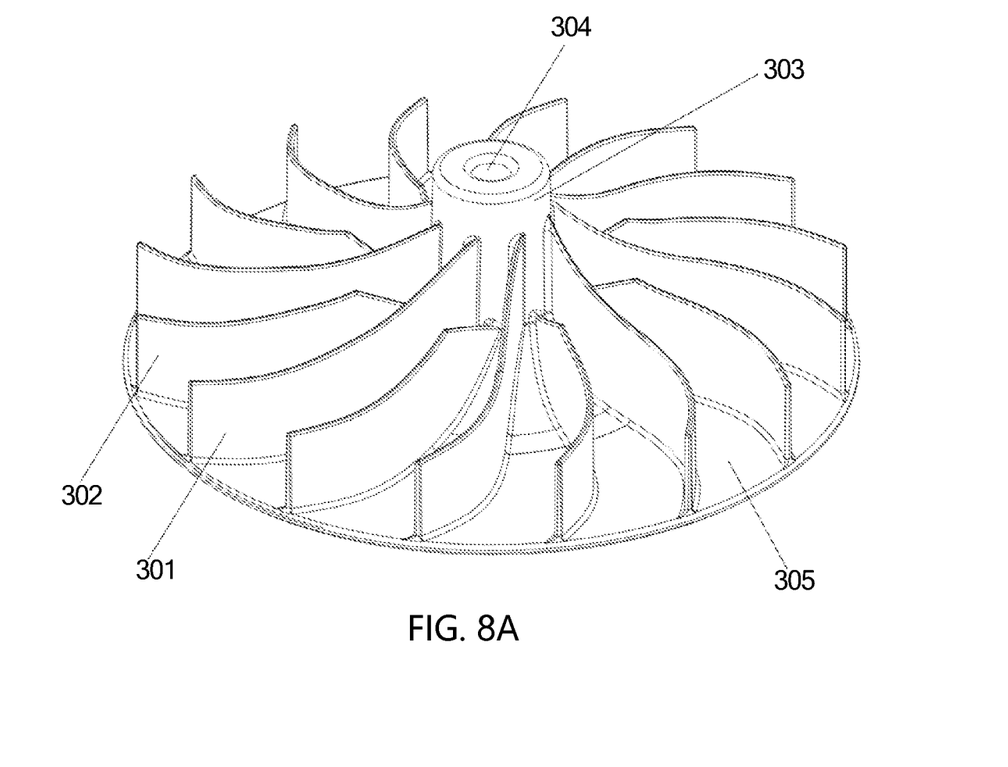
FIG. 8A is the first three-dimensional structure sectional view of the impeller of the present invention.
Figure 8B:
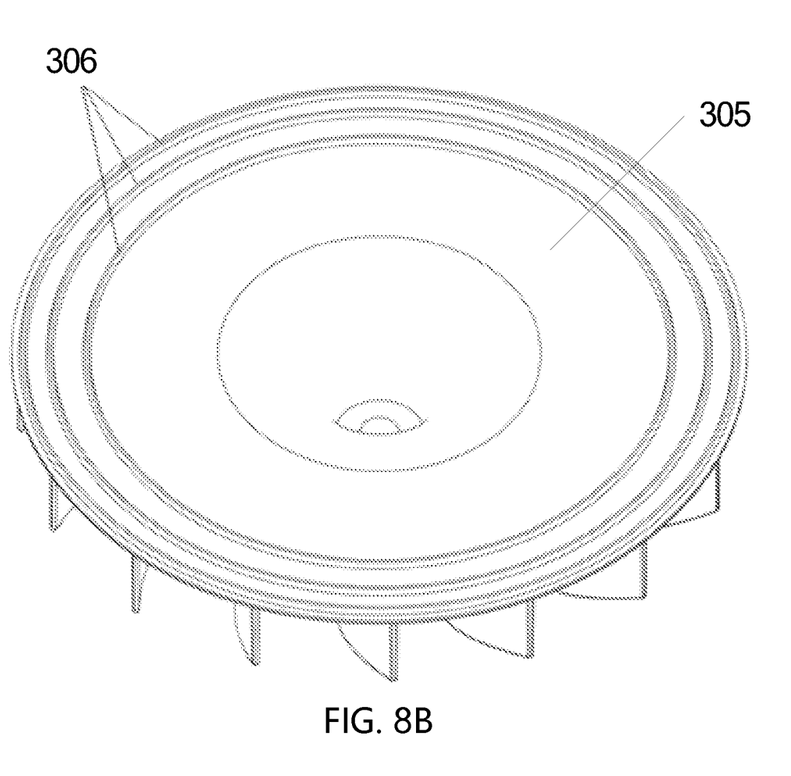
FIG. 8B is second three-dimensional structure sectional view of the impeller of the present invention.
Figure 8C:
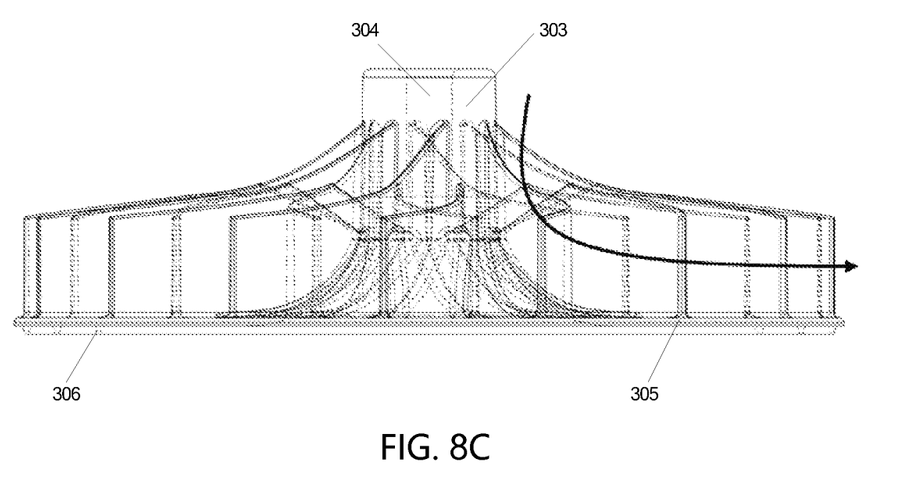
FIG. 8C is third three-dimensional structure sectional view of the impeller of the present invention.

Unlike common impeller 3 installation method where a copper tube is embedded in the impeller 3 and then mounted on motor shaft, in this embodiment, impeller 3 is installed directly on the output shaft 206 of motor 2 in order to reduce total inertia. The meeting part of the motor 2 output shaft 206 and impeller 3 are serrated, increase touching area, to deal with the stress of acceleration and deceleration. The impeller 3 is placed in between the annular frame 404 and top plate 504 of upper enclosure 5. The impeller 3 includes main blades 301, splitter blades 302, wheel-hub 303 and back plate 305. There is a through hole 304 on the center of wheel-hub 303, one end of the wheel-hub 303 connect to the output shaft 206 of motor 2, another end fixed on the center of back plate 305 via structural ribs. On the back plate 305, around the wheel-hub 303, along the circumference direction evenly distributed many main blades 301 and splitter blades 302, the main blades 301 and splitter blades 302 are interlaced. One end of main blade 301 is located on the outer edge of the back plate 305. Another end connected to wheel-hub 303; one end of splitter blade 302 placed outer edge of back plate 305, another end of it has a gap to the wheel-hub 303. The thickness of the back plate 305 in this embodiment of the present invention is limited within 0.8 mm; the number of total number of blades is limited to under 17 (16 in this embodiment), main blade 301 is connected to the wheel-hub 303, the length of splitter blades 302 is ⅔ length of main blades 301. The thickness of splitter blade 302 is limited within 0.8 mm. The impeller 3 in this embodiment constructed with lightest engineering plastic (the density is less than or equal to 1 g/mm$^3$, for example, polypropylene, LDPE, HDPE, TPV etc), and it can also satisfy the stress requirements when the impeller is working at high pressure, high rate of acceleration and deceleration. The diameter of impeller 3 is limited within the 50 mm. In order to prevent impeller 3 that made of low density plastic deforming under stress for a long time, improve the structural strength of the impeller 3, at least one annular protuberance 306 will be on the other side of back plate 305. There are three annular protuberances 306 in this embodiment, and are concentric setting with cross-section shaped inverted triangle.

Figure 9A:
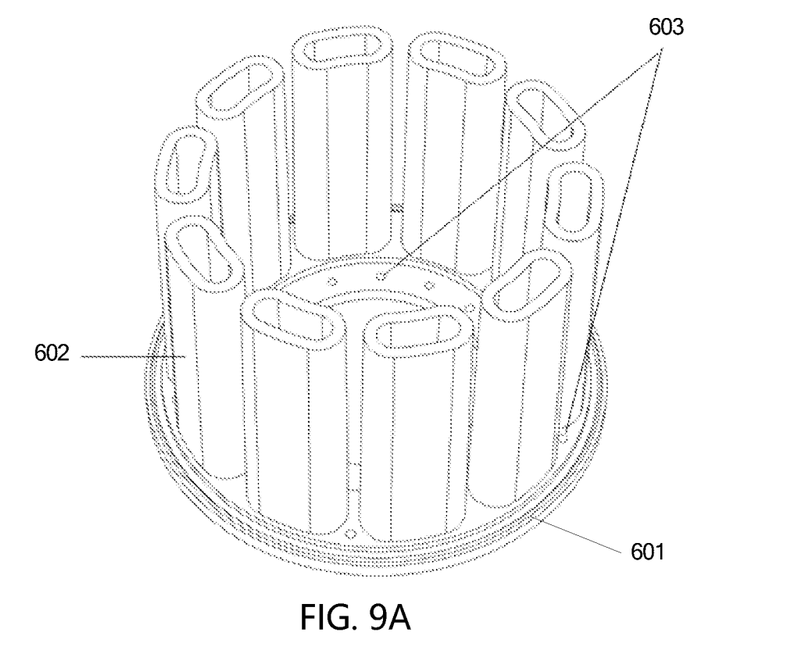
FIG. 9A is first three-dimensional structure sectional view of the air inlet structural part of first embodiment of the present invention.
Figure 9B:
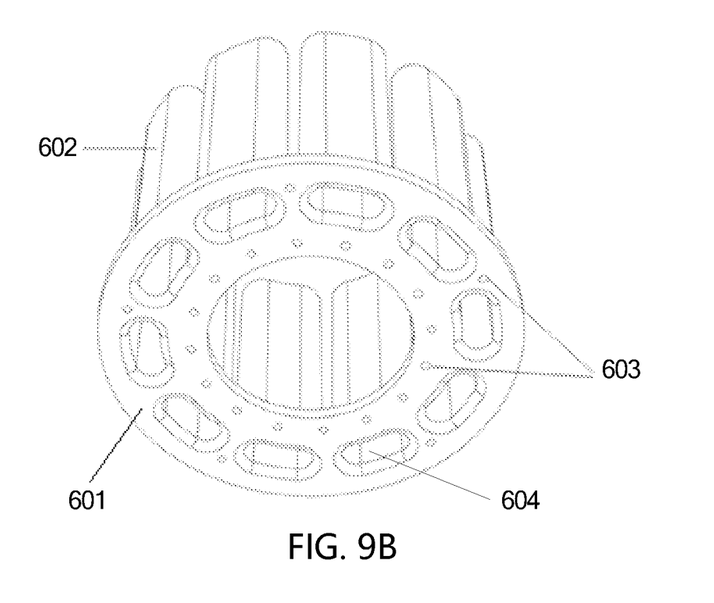
FIG. 9B is second three-dimensional structure sectional view of the air inlet structural part of first embodiment of the present invention.
Figure 10:
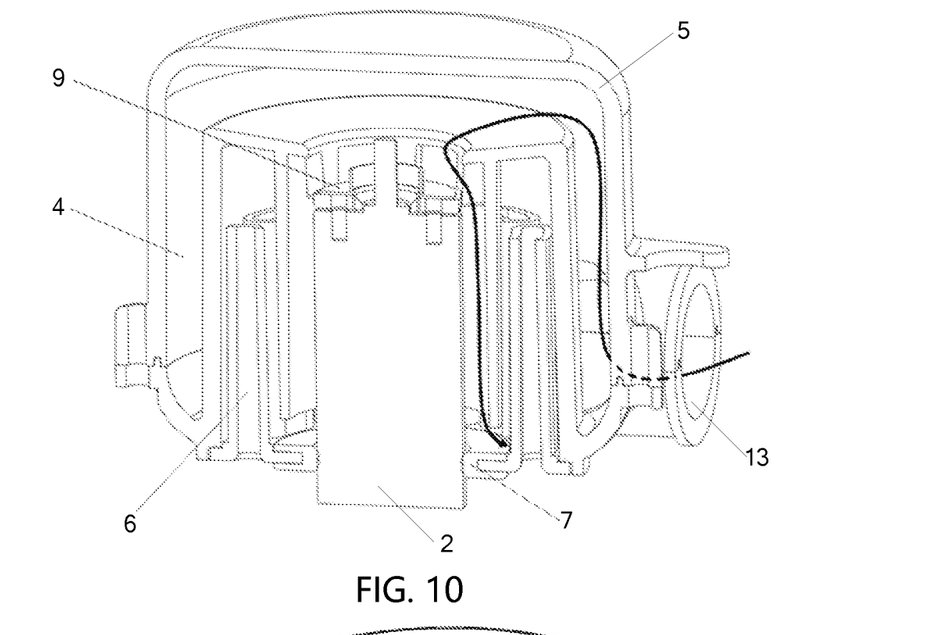
FIG. 10 is an internal structure sectional view of first embodiment of the present invention with impeller removed.

Between the annular wall 401 and outer wall 402, there is an air inlet structure 6 on the lower enclosure, which is coaxial with the motor, and with annular frame 404. The above together forms noise silencing chamber 8, in order to reduce the airflow radiated noise of motor blower 1. The air inlet structure 6 includes flat plate 601 and inlet tube 602. The flat plate 601 is annular and can be affixed to the bottom of lower enclosure by ultrasonic or friction welding. Motor support ring 7 is fixed on the inner hole of flat plate 601. This motor support ring 7 and flat plate 601 together form supporting structure of non-output shaft end of motor 2. The motor support ring 7 in this design is made of soft biomedical compatible flexible silicon, over molded on the flat plate 601. There are number of inlet holes 604 on the flat plate 601 along the circumference direction, each hole has a connected inlet tube 602, and every inlet tube 602 placed in the space between annular wall 401 and outer wall 402. The space between inlet tube 602 top side and the frame 404 forms noise silencing chamber 8. Drainage holes 603 are provided on the flat plate 601.

Figure 11:
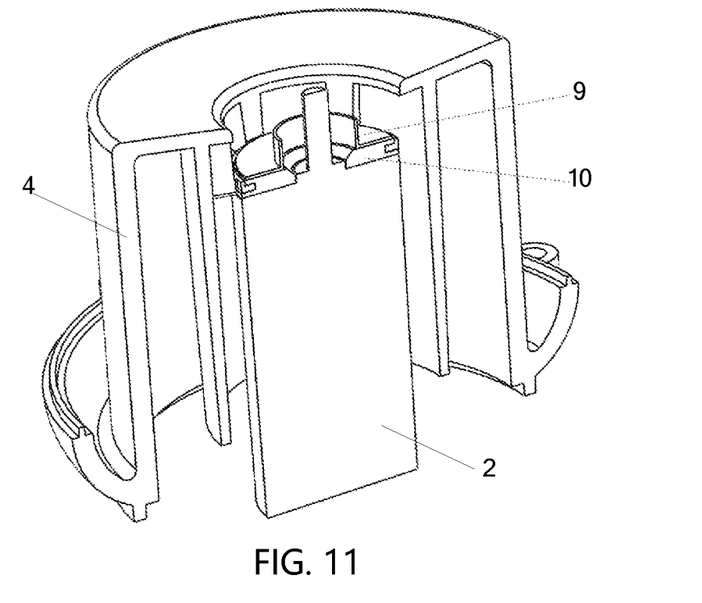
FIG. 11 is an internal structure sectional view of motor mounted to lower enclosure of the present invention.

At the output shaft end of motor 2 (the side connected to the impeller 3), the soft mounting can be used. In this embodiment, the motor 2 is mounted to the motor mounting shelf 407 by a washer 10, which made of a soft material (e.g. silicone). In this way, both ends of motor 2 are "soft" mounted on the housing, which can reduce the unbalanced vibration of rotor and impeller 3 to other parts in the blower 1 that increase radiate noise, then further reduce the total blower noise.

The output shaft end of motor 2 could also be mounted on a water seal circle washer 9. The inner circle extends outwards along axial direction; this water seal washer 9 will reduce the opportunity of water leaking into the bearing 210 part of motor 2, and also act as mounting washer of motor 2.

The output end of shaft of motor 2 is fixed on the motor mounting frame 407 of lower enclosure 4. As shown as FIGS. 6 and 7. The motor 2 includes rotor (includes two pole permanent magnets 207, output shaft made of stainless steel 206 and balancing ring 208), tubular toothless magnetic core of stator 202, tubular coil 203, tubular housing of motor 201, bearing 210, front cover 205 made of aluminum alloy, back cover 204 made of aluminum alloy, wire mount 212, printed circuit board 209, electrical wire 213, bearing preload spring 215 and temperature sensor 211, magnetic core of stator 202 that is fixed with high thermal conductivity of epoxy resin to inside the tubular motor housing 201. The coil 203 is a tubular, three phase two pole toothless. The magnetic core of stator 202 is built by low loss stamped steel sheet, toothless, multi-layered, tubular, and has low thermal resistance. The motor 2 is Brushless DC motor (BLDC). The coil 203 mounted on the inside of magnetic core of stator 202, use high thermal conductivity epoxy resin gluing on the magnetic core of stator 202, forms a low thermal resistance system that can disperse heat from coils 203 and magnetic stator core 202 for effective cooling. The rotor has an ultra-low inertia/power ratio, and the ratio of the length and diameter of non-shaft part of the rotor is 3:1-6:1.

Figure 6:
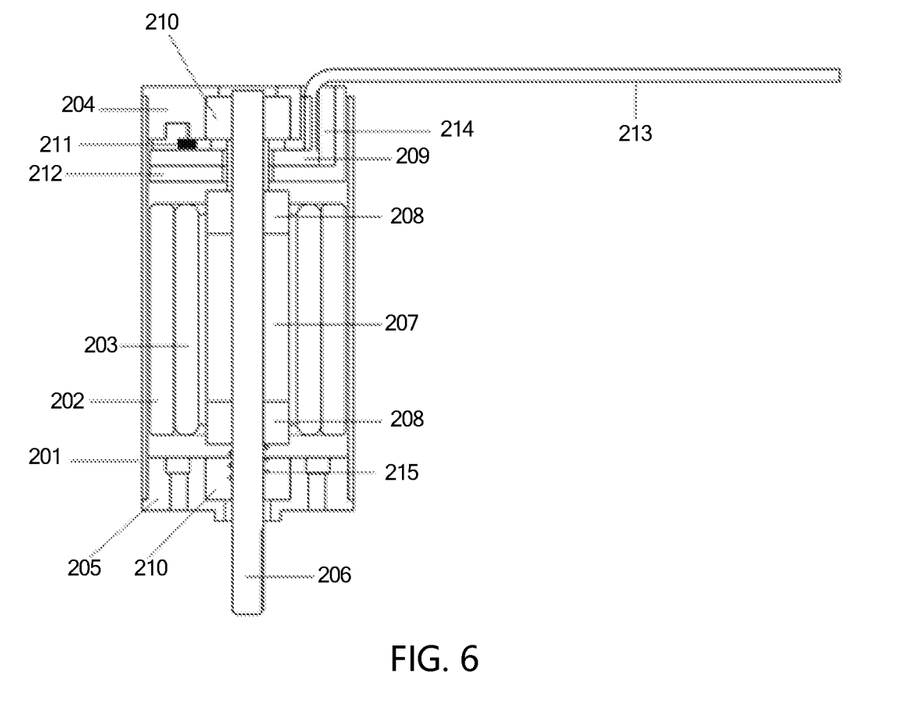
FIG. 6 is an internal structure sectional view of the motor of the present invention.
Figure 7:
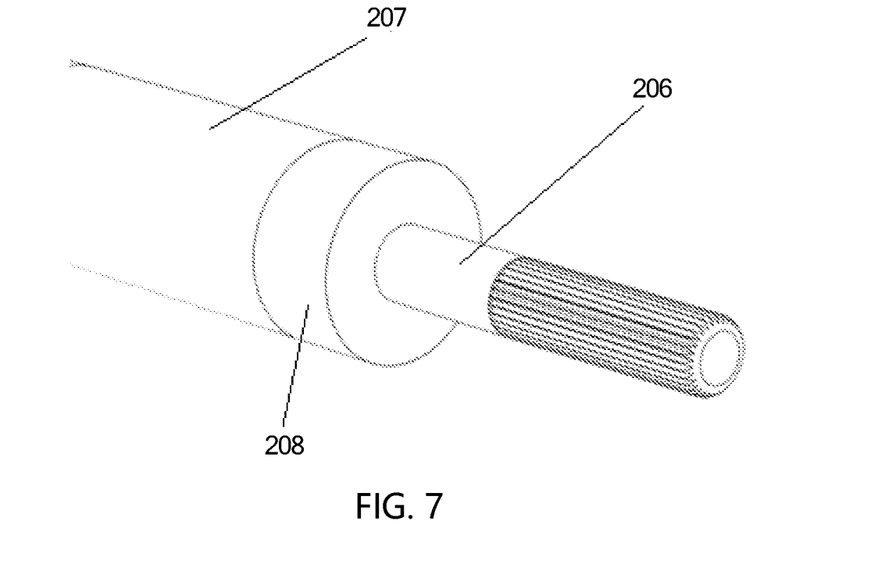
FIG. 7 is an internal structure sectional view of the rotor of the present invention.

The rotor is supported by two bearings mounted between the front cover 205 and back cover 204. Spring 215 provides preloading force to improve rotation accuracy, accurate shaft positioning, eliminate and reduce bearing 210 sliding, provides better control and reduces axial and radial displacements in the load condition such as high speed, high frequency acceleration, deceleration, and also reduce the motor driven blower vibration and noise. preloading on bearing 210 is critical to the performance and life span.

The electrical wire 213 soldered to the printed circuit board 209, the printed circuit board 209 is supported by a wire mount 212 that made of high thermal conductive plastic material. The wire mount 212 is fitted to the tubular motor housing 201 and fixed by heat conduction glue. There are three Y type connected coil terminal wires 214 pass printed circuit board 209, connect to the electrical wire 213, through the electrical wire 213 connect to external driver. The electrical wire 213 is soft flexible type and heat-resistant silicone insulated wire, has low noise, long life cycle and biocompatibility.

The temperature sensor 211 mounted on the printed circuit board 209, high thermal conductively tubular motor housing 201 can conduct heat from other parts of the motor to the temperature sensor 211, so that the temperature sensor can sense the motor's temperature accurately and indirectly, then this temperature signal is sent to the controller (e.g. processor). The printed circuit board 209 substrate is made of high thermal conductivity material (e.g. Aluminum sheet or FR4), and also connect to the electrical wire 213 that is used for temperature monitoring and safety protection of motor 2. The above mentioned motor structure provides low thermal resistance between all heat sources such as magnetic core of stator 202, coil 203, rotor and tubular motor housing 201, and temperature sensor 211. It has two advantages: The first is rapid heat dissipation from motor 2's heat source to tubular motor housing 201, make effective cooling; The second is more accuracy internal temperature sensing for monitoring the motor life and unsafe events, protect patients. In the case of temperature rising, the temperature sensor 211 will provide a high reliable signal to the control center, which is used to control the motor 2 to stop working when the motor 2 temperature is higher than the set value, so as to prevent bearing 210 damage, lubricant drying, end of the motor 2 life, or other safety risks caused by fault events.

In this embodiment, the air outlet 13 of blower 1 horizontal plane is not at same plane as blade of impeller 3. To eliminate tonal noise caused by pressure fluctuations in between the impeller blade and volute tongue. The annular flow channel between the annular wall 501 and outer wall 402 has 1-2° relative to the axial direction. By increasing the cross section area of airflow to transit gradually to the air outlet 13's cross section area.

The working principle of the embodiment:

The blower 1 in this embodiment is a high performance, single-stage axial air inlet, tangential direction air outlet 13. It has built-in noise reduction function. The blower 1 is used as a pressure and flow generator for Bi-level respirators for COPD or severe OSA. High flow treatment device, CPAP or any other respiratory device.

When motor 2 works, it drives the impeller 3 to rotate, the cold gas is driven by the impeller 3 of motor 2 through each inlet tube 602 of air inlet structure 6 along the housing's axial direction enters into the noise silencing chamber 8, then through the motor 2 surface for heat exchange. The curved channel is formed between the outer wall 402 of lower enclosure 4 and annular wall 501 of upper enclosure 5 (as shown in the curved arrow in FIG. 2A), which is used to receive and slow down the air flow from the impeller 3 to generate pressure. In this embodiment, the gas flow output of the impeller 3 is unlike the flow of most existing blower, which flows to the air outlet 13 immediately, instead the compressed airflow will rotate along the center axis of enclosure first, then through the space between annular frame 404 and top plate 504, and flow downwards to the space between outer wall 402 of lower enclosure 4 and annular wall 501 of upper enclosure 5, finally it flows out from air outlet 13; By this way, it can eliminate noise generated by pressure fluctuations between the impeller 3 blade and volute tongue. In this embodiment, structure of impeller 3 can minimize the rotor inertia, so as to improve the response speed of the Bi-level respirator system.

Inlet hole 406 is one of the major noise sources and outwards transmission points of blower 1. The gas flow path of impeller 3 is designed in such a way to: reduce thereby produced noise and gas flow resistance as much as possible due to the interaction between potential non-uniform flow fields, turbulence, turbulence and rigid structure. One of the important sources of noise is sudden changes in flow profile (shape and speed), in order to reduce the noise, slowly changes the flow curve along the inlet flow path (see the arrow in FIG. 8C), and then gas enter the pressure formation zone.

This embodiment, the current popular single large round air inlet hole is replaced by multiple small holes. Gas flow enters the noise silencing chamber 8 through many inlet tube 602, the space between the annular wall 401 and outer wall 402 with inlet tube 602 together forms the gas flow rectifier and noise trap, reduces the inlet flow noise effectively. In order to optimize the noise reduction effect and inlet resistance index, we define all the total inlet tube 602's cross section area is the equivalent area of the blower's cross section area of gas exhaust tube (air outlet 13).

Figure 1:
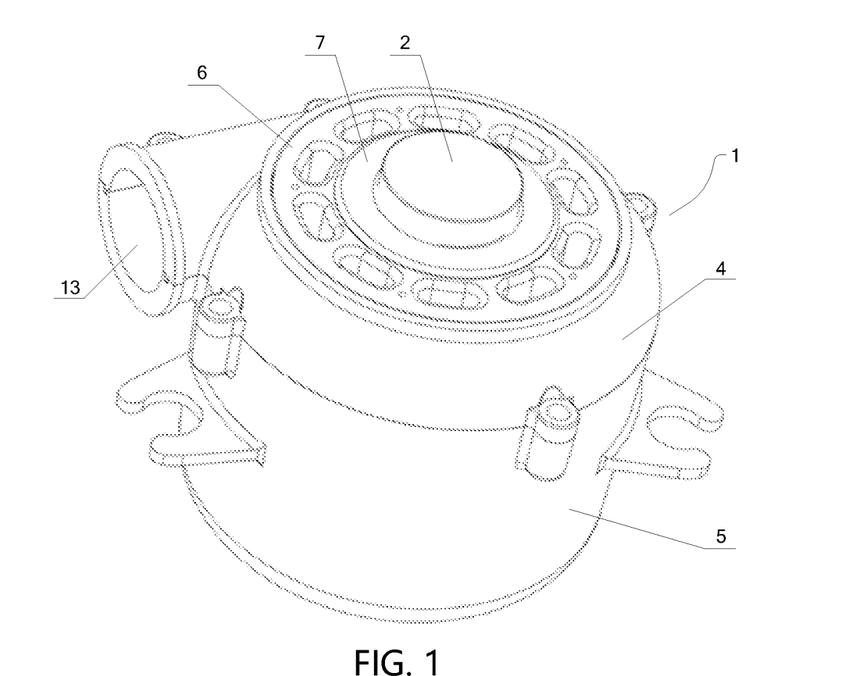
FIG. 1 is a three-dimensional view of the present invention.
Figure 2A:
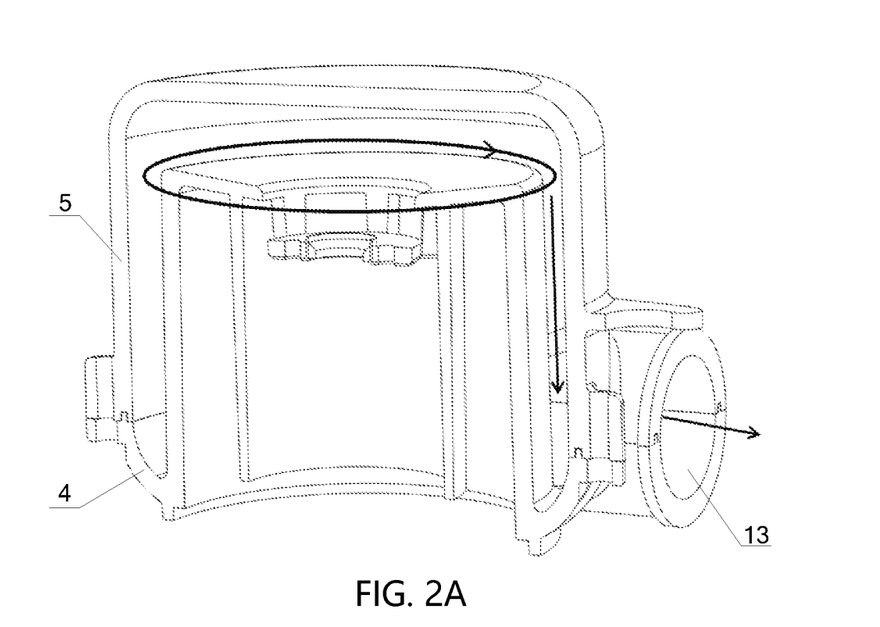
FIG. 2A is a sectional view of the internal structure of the invention that the upper enclosure is coupled to the lower enclosure.
Figure 2B:
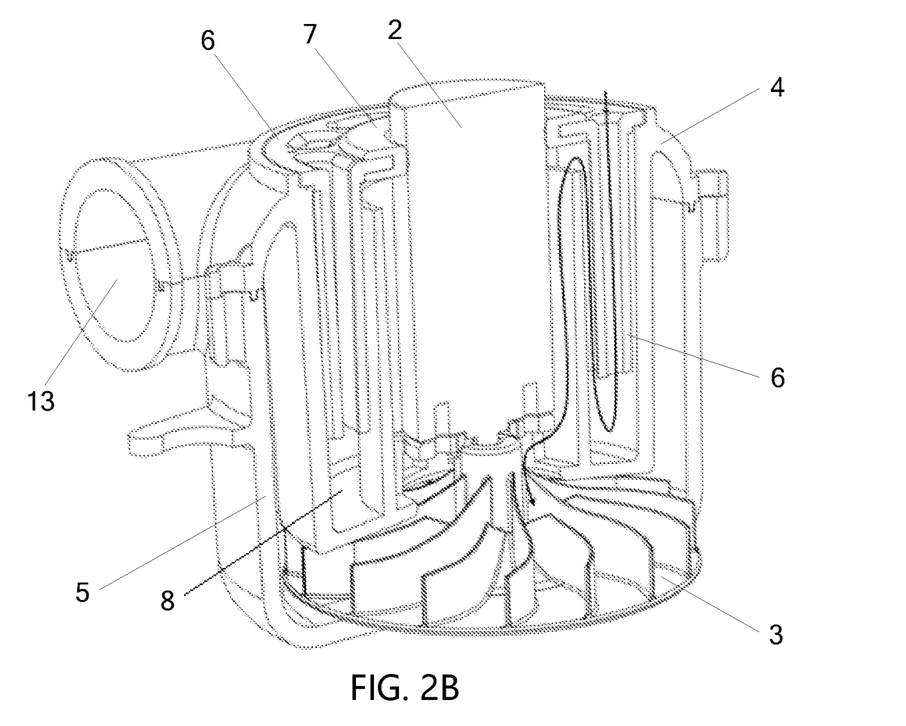
FIG. 2B is a also a sectional view of the internal structure of the first embodiment of the present invention.
Figure 3A:
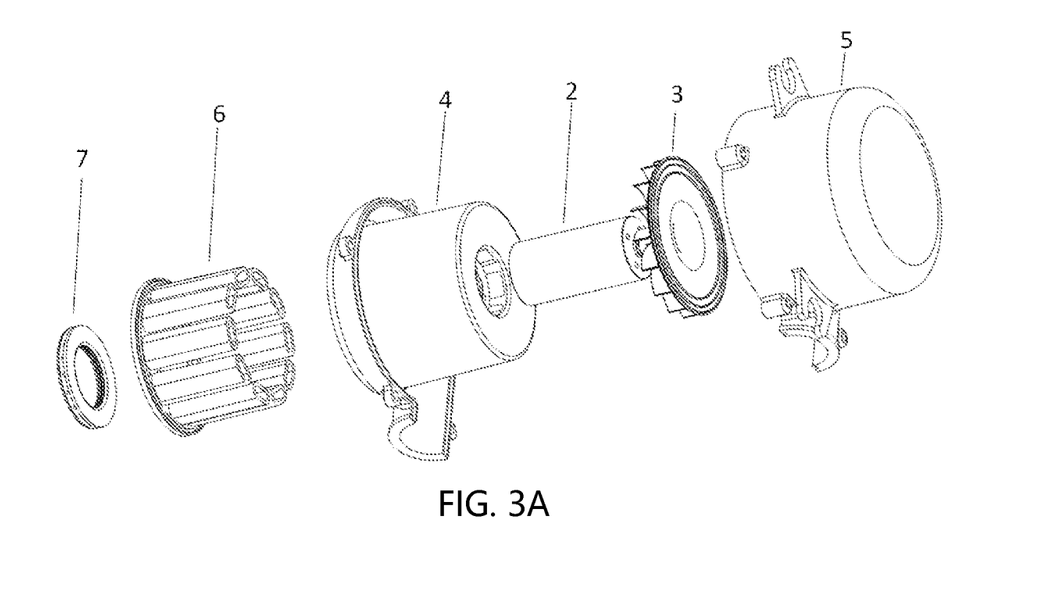
FIG. 3A is exploded view of the first embodiment of present invention.
Figure 3B:
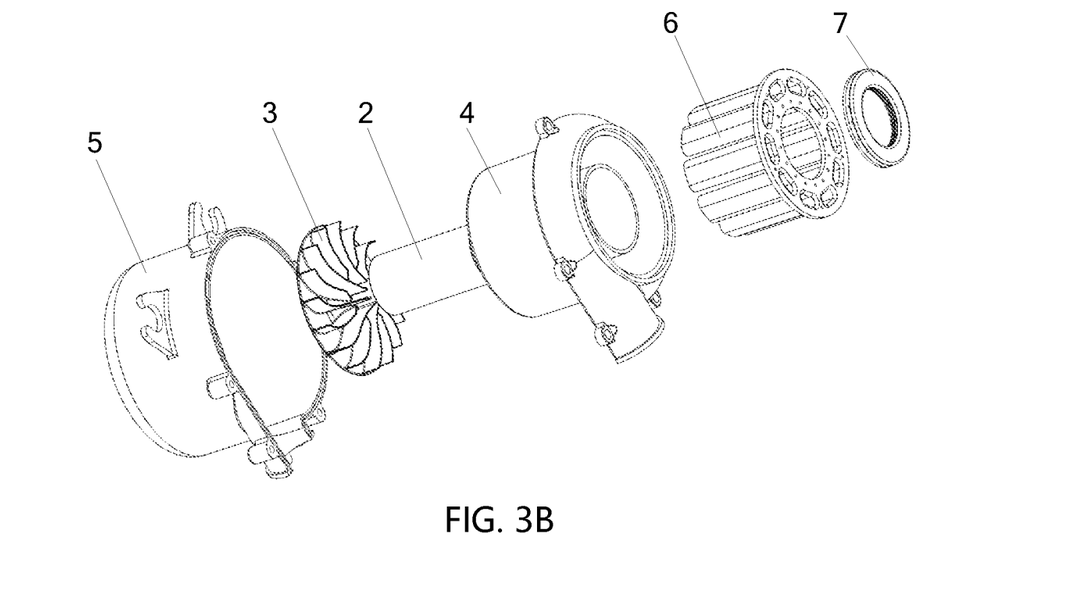
FIG. 3B is second exploded view of first embodiment of present invention.

The inlet airflow from the noise trap region flows along surface of the motor 2, provide effective cooling air for the motor 2 (shown as the arrows in FIG. 2B). The surface of the motor 2 can also be made with fins to further improve the heat exchange rate. The greater the gas movement load of the impeller 3, the greater the heat generated by motor 2. But meanwhile, the added heat will be carried away by increased cold gas flow. Thus, this approach will keep the motor effective cooling under all operation conditions.

A drainage hole 603 in the flat plate 601 provides a drainage solution that when water accidentally pours back into the blower 1 from the humidifier, the water will first fill the space formed between the annular wall 401 and outer wall 402 that could store certain amount of water. If the amount of water poured back exceeds the containing volume, the additional water will flow along the arrow in the FIG. 10, filling the gap between the blower enclosure and drainage hole 603 and slowly draining the water.

Second Embodiment

Figure 12:
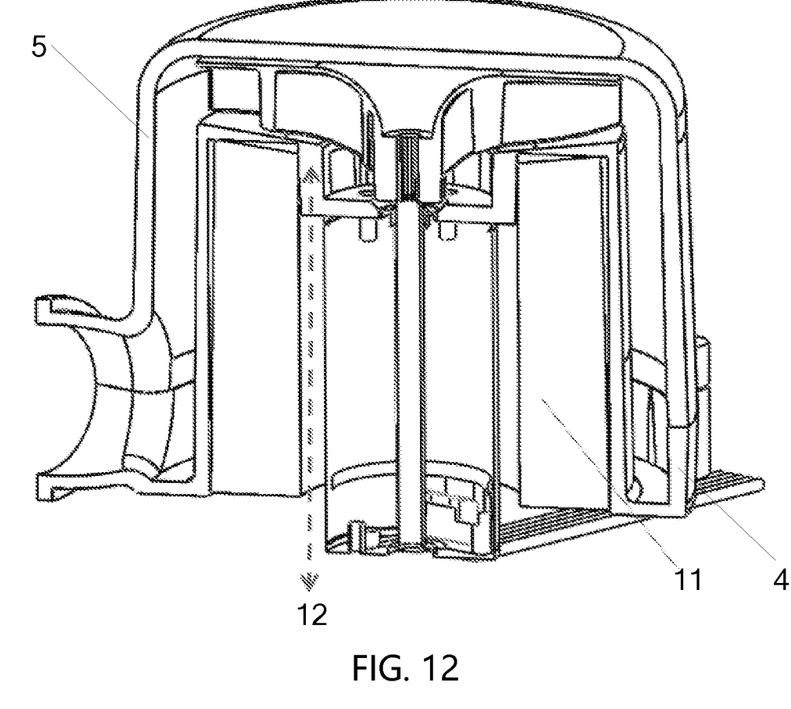
FIG. 12 is another internal structure sectional view of motor mounted to lower enclosure of second embodiment of the present invention.

As shown in FIG.—12, the difference between first embodiment and second embodiment is that the second embodiment removed the air inlet structure 6, instead the sound absorbing foam 11 is mounted on the inner face of annular wall 401 of the lower enclosure 4. The air inlet channel 12 is formed in between the sound absorbing foam 11 and outer surface of motor 2. The outside air enters from bottom of lower enclosure 4, heat is exchanged with the surface of motor 2 through air inlet channel 12, the sound absorbing foam can reduce the noise. In the second embodiment, the sound absorbing foam is made of PE or EVA open foaming, the sound absorption coefficient of the air inlet sound absorbing foam is 0.8-1 between the frequency of 500-4 KHz.

The blower provided by this invention can be applied to where the fast response time, easy to drive and control, higher output pressure, high flow rate, safety and high reliability, low noise, small size, low cost pressurized treatment gas source is required, for example, BiPAP.

We claim:

1. A blower for a respirator device, comprising: a motor (2), an impeller (3), a lower enclosure (4), and an upper enclosure (5),
   wherein the lower enclosure (4) is coupled to the upper enclosure (5) and cooperatively form an air outlet (13),
   a first end of the lower enclosure (4) is open to an exterior and a second end of the lower enclosure (4) has an annular frame (404) extending into the upper enclosure,
   the motor (2) is disposed inside the lower enclosure (4) and an output shaft (206) of the motor is connected to an impeller (3) disposed in a space between the annular frame (404) of the lower enclosure (4) and a top plate (504) of the upper enclosure (5), and
   an air passage begins at the first end of the lower enclosure (4) to the impeller (3) and ends at the air outlet (13).

2. The blower according to the claim 1, wherein an air inlet structural member (6) is disposed at the first end of the lower enclosure (4) and serves as a starting point of the air passage, the air inlet structural member comprises a flat plate (601) and an air inlet tube (602), the flat plate is annular in shape and is mounted on the lower enclosure (4), a plurality of inlet holes (604) are disposed along the circumferential direction on the flat plate (601), and a bottom of inlet tube (602) is fluidly connected to the plurality of inlet holes (604) and forms a noise silencing chamber (8) with the annular frame (404).

3. The blower according to the claim 2, wherein the flat plate (601) has a plurality of drainage holes (603) arranged thereon.

4. The blower according to the claim 2, wherein the flat plate (601) has a motor support ring (7), and the motor support ring (7) and the flat plate (601) cooperate to form a motor supporting structure of a non-output shaft end of the motor (2).

5. The blower according to claim 1, further comprising a sound absorbing foam disposed inside the lower enclosure (4), wherein the sound absorbing foam and an outer surface of the motor forms an air inlet channel (12) that is a portion of the air passage.

6. The blower according to claim 5, wherein the sound absorbing foam (11) is made of PE or EVA open foaming.

7. The blower according to claim 5, wherein of the sound absorption coefficient of sound absorbing foam (11) is between 0.8 to 1 when a frequency is between 500 to 4 KHz.

8. The blower according to claim 5, wherein a length to diameter ratio of a non-shaft part of a rotor of the motor (2) is between 3:1 to 6:1.

9. The blower according to claim 5, wherein a tubular housing of the motor (2) is made of a thermally conductive material.

10. The blower according to claim 9, wherein the tubular motor housing (201) of the motor (2) is made of an aluminum alloy.

11. The blower according to claim 9, wherein a motor coil (203) is slot-less tubular in shape, and is mounted on a magnetic core of a stator (202) mounted on the tubular motor housing (201) of the motor (2).

12. The blower according to claim 1, wherein the motor (2) is equipped with a temperature sensor (211).

13. The blower according to claim 1, wherein the output shaft (206) of the motor (2) has a water-proof washer (9) and/or a soft washer (10).

14. The blower according to claim 1, wherein the impeller (3) is made of a material having a density of less than 1 g/mm$^3$.

15. The blower according to claim 1, wherein a back plate of the impeller (3) has at least one annular protuberance (306).

16. The blower according to claim 1, wherein the impeller (3) is affixed to the output shaft (206) of the motor (2) directly, a portion of the output shaft (206) that is in contact with the impeller (3) is serrated.

17. The blower according to claim 1, wherein the lower enclosure (4) has an annular wall (401) and an outer wall (402), a lower end of the annular wall (401) and a lower end of the outer wall (402) are open, an upper end of the annular wall (401) and an upper end of the outer wall (402) are provided with the annular frame (404), a space between the outer wall (402) and the upper enclosure (5) forms a gas path to the air outlet (13), the motor (2) is disposed on an inner side of the annular wall.

18. The blower according to claim 1, wherein an inner ring of the annular frame (404) extends downward to form a plurality of support ribs (405), a space between two adjacent support ribs of the plurality of support ribs (405) forms an inlet hole (406), an inner side of an annular wall (401) has a motor mounting frame (407), which is connected to the plurality of support ribs (405), the output shaft of the motor (2) is affixed on the motor mounting frame (407); an outer edge of the outer wall (402) a portion of an outlet channel (403).

19. The blower according to claim 1, wherein the upper enclosure (5) has an annular wall (501), an outlet channel (502), and a top plate (504), the annular wall (501) is mounted to the lower enclosure (4) on an external surface of an outer wall (402), and an outer edge of the annular wall (501) forms a portion of the outlet channel (502).

20. The blower according to claim 1, wherein an annular flow channel between an annular wall (501) and an outer wall (402) has 1 to 2 degree angle relative to an axial direction of the upper enclosure (5).

* * * * *